United States Patent
Haik

(10) Patent No.: US 7,527,980 B2
(45) Date of Patent: May 5, 2009

(54) INDIRECT DETECTION OF CARDIAC MARKERS FOR ASSESSING ACUTE MYOCARDIAL INFARCTION

(75) Inventor: Yousef Haik, Tallahassee, FL (US)

(73) Assignee: Florida State University Research Foundation, Tallahassee, FL (US)

( * ) Notice: Subject to any disclaimer, the term of this patent is extended or adjusted under 35 U.S.C. 154(b) by 510 days.

(21) Appl. No.: 11/204,463

(22) Filed: Aug. 16, 2005

(65) Prior Publication Data
US 2006/0040412 A1   Feb. 23, 2006

Related U.S. Application Data

(60) Provisional application No. 60/602,420, filed on Aug. 18, 2004.

(51) Int. Cl.
*G01N 33/543* (2006.01)
*G01N 33/567* (2006.01)

(52) U.S. Cl. .................. 436/526; 436/518; 435/7.1; 435/7.5; 435/7.7; 435/7.72; 435/7.94; 435/14

(58) Field of Classification Search ............... 436/536, 436/518; 435/7.1, 7.5, 7.7, 7.72, 7.94, 14
See application file for complete search history.

(56) References Cited

U.S. PATENT DOCUMENTS

| 6,132,607 | A | 10/2000 | Chen et al. |
| 2002/0106708 | A1* | 8/2002 | Thomas et al. ............ 435/7.93 |
| 2004/0065969 | A1 | 4/2004 | Chatterjee et al. |
| 2004/0146529 | A1 | 7/2004 | Chen et al. |

OTHER PUBLICATIONS

Abdel-Hamid, et al., "Flow-through immunofiltration assay system for rapid detection of E. coli O157:H7," Biosensors & Bioelectronics, 14:309-16 (1999).
Achar, et al., "Diagnosis of acute coronary syndrome," American Family Physician, 72(1):119-126 (2005).
Adams, et al., "Biochemical markers of myocardial injury. Is MB creatine kinase the choice for the 1990s?," Circulation, 88(2):750-763 (1993).
Adams, "Clinical application of markers of cardiac injury: basic concepts and new considerations," Clinica Chimica Acta, 284:127-134 (1999).

(Continued)

Primary Examiner—Mark L Shibuya
Assistant Examiner—Pensee T Do
(74) Attorney, Agent, or Firm—Sutherland Asbill & Brennan LLP

(57) ABSTRACT

Assay systems and methods are provided for detecting a target antigen in a physiological fluid (e.g., blood, serum, or urine). The method includes linking via a first antibody a magnetic microparticle to the target antigen in the physiological fluid; linking via a second antibody a glucose molecule to the target antigen; utilizing a magnetic field to separate the magnetic microparticle-linked antigen from the physiological fluid to form a test sample; and detecting the glucose in the test sample to determine the concentration of target antigen in the physiological fluid. The target antigen can be a protein or marker resulting from cardiac tissue injury, which can be used to assess acute myocardial infarction. An exemplary target antigen is myoglobin. The glucose detection preferably is one that can be done rapidly, e.g., with a conventional glucometer, and may include measuring the electrical resistance, color, or pH of the test sample.

28 Claims, 2 Drawing Sheets

OTHER PUBLICATIONS

Bayliss, "*MAFF Research Program FS 12, Detection and Separation of Pathogens and their Toxins,*" MAFF UK, Center for Applied Microbiology and Research, Porton Down (1999).

Berroeta, et al., "*The use of cardiac troponins (T or I) measurement in cardiology and various clinical setting,*" Ann Fr Anesth Reanim, (2005).

Chatterjee, et al., "*Size dependent magnetic properties of iron oxide nanoparticles,*" Journal of Magnetism and Magnetic Materials, 257:113-118 (2003).

Chen, et al., "*Role of heart-type fatty acid binding protein in early detection of acute myocardial infarction in comparison with cTnI, CK-MW and myoglobin,*" Journal of Huazhong University of Science and Technology [Med Sci], 24(5):449-51, 459 (2004).

Cole, et al., "*The EBV-hybridoma technique and its application to human lung cancer,*" Monoclonal Antibodies and Cancer Therapy, pp. 77-96 (1985).

Cubrilo-Turek, et al., "*New biochemical markers in the assessment of minor myocardial damage in critically ill patienst,*" Acta Med Croatica, 58(5):381-8 (2004).

DeWinter, et al., "*Value of myoglobin, troponin T, and CK-MB$_{mass}$ in ruling out an acute myocardial infarction in the emergency room,*" Circulation, 92:3401-3407 (1995).

Eggers, et al., "*Combining different biochemical markers of myocardial ischemia does not improve risk stratification in chest pain patients compared to troponin I alone,*" Coronary Artery Disease, 16(5):315-19 (2005).

Eggers, et al., "*Diagnostic value of serial measurement of cardiac markers in patients with chest pain: limited value of adding myoglobin to troponin I for exclusion of myocardial infarction,*" American Heart Journal, 148(4):574-581 (2004).

Eisenman, et al., "*Are all troponin assays equivalent in the emergency department?,*" Singapore Med. J., 46(7):325-327 (2005).

Feldsine, et al., "*Visual immunoprecipitate Assay (VIP) for detection of enterohemorrhagic Escherichia coli (EHEC) O157:H7 in selected foods: collaborative study,*" Journal of AOAC International, 80(3):517-29 (1997).

Galfre, et al.., "*Antibodies to major histocompatibility antigens produced by hybrid cell lines,*" Nature, 266:550-52 (1977).

Galvani, et al., "*New markers for early diagnosis of acute myocardial infarction,*" International Journal of Cardiology, 65(Suppl.1):S17-S22 (1998).

Gefter, et al., "*A simple method for polyethylene glycol-promoted hybridization of mouse myeloma cells,*" Somatic Cell Genet., 3:231-36 (1977).

Gibler, et al., "*Early detection of acute myocardial infarction in patients presenting with chest pain and nondiagnostic ECGs: Serial CK-MB sampling in the emergency department,*" Annals of Emergency Medicine, 19:1359-66 (1990).

Haik, et al., "*Development of magnetic device for cell separation,*" Journal of Magnetism and Magnetic Materials, 194:254-61 (1999).

Héden, et al., "*Acute myocardial infarction detected in the 12-lead ECG by artificial neural networks,*" Circulation, 96:1798-1802 (1997).

Hedges, et al, "*Serial ECGs are less accurate than serial CK-MB results for emergency department diagnosis of myocardial infarction,*" Annals of Emergency Medicine, 21(12):1445-50 (1992).

Hudson, et al., "*Cardiac markers: point of care testing,*" Clinica Chimica Acta, 284:223-237 (1999).

Ishii, et al., "*Prognostic value of serum concentration of heart-type fatty acid-binding protein relative to cardiac troponin T on admission in the early hours of acute coronary syndrome,*" Clinincal Chemistry, 51(8):1397-1404 (2005).

Johnson, et al., "*Comparison of the BAX for screening/E.coli O157:H7 method with conventional methods for detection of extremely low levels of Escherichia coli O157:H7 in ground beef,*" Applied and Environmental Microbiology, 64(11):4390-95 (1998).

Kennett, et al., "*Monoclonal antibodies: a new dimension in biological analyses,*" Plenum Press: New York and London (1980).

Kim, et al., "*Use of chicken egg-yolk antibodies against K88+fimbrial antigen for quantitative analysis of enterotoxigenic Escherichia coli (ETEC) K88+ by a sandwich ELISA,*" Journal of the Science of Food and Agriculture, 79:1513-18 (1999).

Kohler, et al., "*Continuous cultures of fused cells secreting antibody of predefined specificity,*" Nature, 256:495-97 (1975).

Kozbor, et al., "*The production of monoclonal antibodies from human lymphocytes,*" Immunology Today, 4(3):72-79 (1983).

Lerner, "*How to make a hybridoma,*" The Yale Journal of Biology and Medicine, 54:387-402 (1981).

Lin, et al., "*Rates of positive cardiac troponin I and creatine kinase MB mass among patients hospitalized for suspected acute coronary syndromes,*" Clinical Chemistry, 50(2):333-38 (2004).

McCarthy, et al., "*Missed diagnosis of acute myocardial infarction in the emergency department: Results from a multicenter study,*" Annals of Emergency Medicine, 22(3):579-82 (1993).

Ogunjimi, et al., "*Adsorption of endogenous polyphenols relieves the inhibition by fruit juices and fresh produce of immuno-PCR detection of Escherichia coli 0157:H7,*" FEMS Immunology and Medical Microbiology, 23:213-20 (1991).

Padhye, et al., "*Production and characterization of a monoclonal antibody specific for enterohemorrhagic Escherichia coli of serotypes O157:H7 and O26:H11,*" Journal of Clinical Microbiology, 29(1):99-103 (1991).

Panteghini, "*Diagnostic application of CK-MB mass determination,*" Clinica Chimica Acta, 272:23-31 (1998).

Penttila, et al., "*Myoglobin, creatine kinase MB isoforms and creatine kinase MB mass in early diagnosis of myocardial infarction in patients with acute chest pain,*" Clinical Biochemistry, 35:647-53 (2002).

Puleo, et al., "*Use of a rapid assay of subforms of creatine kinase MB to diagnose or rule out acute myocardial infarction,*" New England Journal of Medicine, 331(9): 561-66 (1994).

Roberts, et al., "*Earlier diagnosis and treatment of acute myocardial infarction necessitates the need for a 'new diagnostic mind-set',*" Circulation, 89(2):872-881 (1994).

Sallach, et al., "*A change in serum myoglobin to detect acute myocardial infarction in patients with normal troponin I levels,*" American Journal of Cardiology, 94:864-867 (2004).

Shelton, et al., "*Evaluation of parameters affecting quantitative detection of Escherichia coli O157 in enriched water samples using immunomagnetic electrochemiluminescence,*" Journal of Microbiological Methods, 55:717-25 (2003).

Suter, et al., "*The immunochemistry of sandwich elisas—III. The stoichiometry and efficacy of the protein-avidin-biotin capture (PABC) system,*" Molecular Immunology, 26(3):221-30 (1989).

Van Nieuwenhoven, et al., "*Discrimination between myocardial and skeletal muscle injury by assessment of the plasma ratio of myoglobin over fatty acid-binding protein,*" Circulation, 92:2848-54 (1995).

Vote, et al., "*Blood glucose meter performance under hyperbaric oxygen conditions,*" Clinica Chimica Acta, 305:81-87 (2001).

Wodzig, et al., "*Estimation of myocardial infarct size from plasma myoglobin or fatty acid-binding protein. Influence of renal function,*" European Journal of Clinical Chemistry and Clinical Biochemistry, 35(3):191-98 (1997).

Wright, et al., "*Immunomagnetic separation as a sensitive method for isolating Escherichia coli O157 from food samples,*" Epidemiology and Infection, 113:31-39 (1994).

Yu, et al., "*Development of a magnetic microplate chemifluorimmunoassay for rapid detection of bacteria and toxin in blood,*" Analytical Biochemistry, 261:1-7 (1998).

Yu, et al., "*Immunomagnetic-electrochemiluminescent detection of Escherichia coli O157 and Salmonella typhimurium in foods and environmental water samples,*" Applied and Environmental Microbiology, 62(2):587-92 (1996).

\* cited by examiner

INDIRECT DETECTION OF CARDIAC MARKERS FOR ASSESSING ACUTE MYOCARDIAL INFARCTION

CROSS-REFERENCE TO RELATED APPLICATIONS

This application claims the benefit of U.S. Provisional Application No. 60/602,420, filed Aug. 18, 2004. The application is incorporated herein by reference in its entirety.

BACKGROUND OF THE INVENTION

This invention relates generally to diagnostic immunoassays for medical applications, and more particularly to methods for rapidly determining whether a person has suffered an acute myocardial infarction.

Acute Myocardial Infarction (AMI), commonly referred to as a heart attack, is a disorder in which a region of the heart muscle is damaged due to an inadequate supply of oxygen thereto. For instance, a clot in a coronary artery that blocks the supply of oxygen to the particular region of the heart and results in death or damage to the cells in this region can cause an AMI. Typically, the AMI occurs as a result of a coronary artery that has been narrowed due to the effects of arteriosclerosis. The damaged tissue causes a permanent loss of contraction of this portion of the heart muscle.

There is a great desire for early determination as to whether AMI is occurring for patients that present themselves at an emergency room of a hospital. A significant number of patients complain from chest pain and/or other symptoms concomitant with AMI (Hedén et al., *Circulation*, 96:1798-802 (1997)). This early determination allows hospital personnel to determine which patients can be sent home and which patients have suffered an AMI. For patients who have suffered an AMI, thrombolytic therapy should be started as soon as possible after the AMI for maximum benefit. Unfortunately, a high percentage of patients who present with chest pains are admitted to the intensive care unit or telemetry ward of the hospital. In addition, a small percentage of patients that are sent home after the clinicians determined such patients did not suffer an AMI, shortly thereafter are admitted to the hospital as having suffered an AMI. These problems are due to traditional diagnostic regiments lacking sufficient sensitivity in a large portion of the cases presented.

Currently, electrocardiographs (ECG) are used in concert with blood serum protein elevations to diagnose the infarction. It has been shown that the diagnostic sensitivity of an ECG is approximately 50% in determining myocardial damage (Gibler et al., *Ann Emerg Med.* 19:1359-66 (1990)). The number of individuals who have been discharged from emergency departments provides further evidence of the need for a more efficient method of AMI detection. It has been indicated that approximately 25% of the patients sent home with an acute myocardial infarction had ST elevations that were misjudged or overlooked by the physician (McCarthy et al., *Ann Emerg Med* 22:579-82 (1993)). In addition, an estimated 80% of the patients admitted to the coronary care unit for suspected acute myocardial infarction are discharged without having this diagnosis confirmed (Puleo et al., *N Engl J Med,* 331:561-66 (1994); Roberts & Kleiman, *Circulation,* 89(2): 872-81 (1994)). More importantly, 2-8% of the 2 million individuals that were not admitted developed AMIs, resulting in added injury to the individual and malpractice actions taken against the institution (Hudson et al., *Clinica Chimica Acta,* 284(2):223-37 (1999)).

Due to the increasing number of AMI patients accompanied with a difficulty in diagnosing the anomaly, a major push to develop innovative approaches to tackle the recognition of myocardial infarctions has been noticed. Most of these advances utilize immunoassays to decrease the time of AMI detection, granting the patient a better chance of survival (Hudson et al., *Clinica Chimica Acta* 284:223-37 (1999)).

The release of specific cardiac proteins from the injured cardiac tissue into the patient's bloodstream has become an important parameter for the diagnosis of AMI. A proper protein marker to use in such an assay is one that is present in measurable concentrations in the early AMI onset stage as well as having high clinical sensitivity and specificity (De Winter et al., *Circulation,* 92(12):3401-07. Several proteins or markers can result from the cardiac tissue injury. Myoglobin, creatine kinase, fatty acid-binding protein (FACB), cardiac specific troponins, and glycogen phosphorylase (AP) are released into the blood stream immediately after the cardiac injury. The measurement of these markers has become an increasingly important for the diagnosis and sizing of AMI. Depending on the differences in their concentration in the blood stream, these markers are used both for diagnosis, by detecting the presence of increase concentration of these proteins in patients who have AMI signs, and sizing of an AMI, by taking serial measurements of these markers to estimate the extent of damage (Adams et al., *Circulation,* 88(2):750-63 (1993)).

An ideal marker that could be used to detect myocardial injury would possess a number of characteristics. It must have high protein concentrations within the myocardium, while being present in low concentrations in noncardiac tissue. It also should be rapidly released after cardiac injury, persists in plasma, and allow the development of accurate and rapid assays (Adams, *Clinica Chimica Acta* 284(2):127-34 (1999)).

The CK-MB *isoenzyme* (86 kDa) is one of the most common markers used for the evaluation of patients with suspected AMI (Achar et al., *Am. Fam. Physician* 72(1):119-26 (2005)). Damaged myocardial tissue releases CK-MB in a characteristic fashion following the injury, allowing clinicians to often determine the timing and extent of an AMI, with the concentration level of CK-MB normally being 3 U/L and peaking at over 25 U/L 16-20 hours after infarction. Unfortunately, CK-MB is insufficiently sensitive during the early phases of an AMI, with an increase in concentration also present during massive skeletal muscle damage. The late peak of CK-MB concentration has led to its primary use in confirming an AMI at 24 hours post-injury (Id.; Cubrilo-Turek et al., *Acta Med Croatica* 58(5):381-8 (2004); Gibler et al., *Ann Emerg Med* 19:1359-66 (1990)). Recently, the use of the two CK-MB subforms (CK-MB 1 and CK-MB 2) has been proposed for a more accurate diagnosis of early AMI. CK-MB 2 is found in myocardial tissue, and upon tissue destruction is released into the blood as the more negatively charged subform, CK-MB 1. A level of CK-MB>1 U/L and a ratio of CK-MB 2 to CK-MB 1>1.5 has been reported to have a better sensitivity within the first six hours post-AMI compared to CK-MB alone (Penttila et al., *Clin Biochem* 35(8):647-53 (2002); Lin et al., *Clin Chem* 50(2):333-38 (2004)). Troponin is a protein also found in the skeletal and cardiac muscle that has become a standard marker for the diagnosis of AMI (Achar et al., *Am Fam Physician* 72(1):119-26 (2005); Berroeta et al., *Ann Fr Anesth Reanim, (*2005)). Used in conjunction with CK-MB, troponin can detect not only minor myocellular necrosis but also can be used as an indicator for patients at risk for ACS [Penttila et al., *Clin Biochem* 35(8): 647-53 (2002); Lin et al., *Clin Chem* 50(2):333-38 (2004);

Berroeta et al., *Ann Fr Anesth Reanim*, 2005)). Troponin entails three forms (C, I, and T) which along with actin and myosin regulate muscle contraction. While troponin C is identical in cardiac and skeletal muscles, troponins I and T are site specific. Therefore, a rise in cardiac specific troponin I and T is suggestive for myocardial damage. Both forms rise within the first 3-4 h of the injury, peak generally within 24 h, and remain elevated for 10-14 days, therefore qualifying as late markers for a recent AMI in patients who do not receive an immediate medical assistance. Although troponin I and T have similar sensitivity and specificity for the detection of myocardial infarction, troponin T may be elevated under other pathological conditions such as renal failure or polymyositis. Recently, the use of troponin I over the T isoform in the diagnosis of ACS and AMI has been reported (e.g., Eisenman et al., *Singapore Med. J.* 46(7):325-27 (2005). Moreover, troponin I alone has been shown to be a better marker for risk stratification in patients with chest pain than when combined with CK-MB and myoglobin (Eggers et al., *Am Heart J.* 148(4):574-81 (2004); Eggers et al., *Coron Artery Dis* 16(5): 315-19 (2005)). Recent studies have shown that FABP and myoglobin can be used to detect a myocardial injury sooner after an infarction than CK-MB or troponin T (Achar et al., *Am Fam Physician* 72(1):119-26 (2005); Ishii et al., *Clin Chem* (2005); Chen et al., *J. Huazhong Univ Sci Technolog Med Sci* 24(5):449-51, 459 (2004); Sallach et al., *Am J. Cardiol* 94(7):864-67 (2004)). Myoglobin (17 kDa) and FABP (15 kDa) are two small cardiac proteins that show elevated serum levels soon after the infarction, significantly increasing their concentration within 2 hours after infarction and peeking 4-6 hours after an infarction. The concentrations of myoglobin and FABP in plasma rise from about 32 μg/L and 3 μg/L respectively to over 200 μg/L for myoglobin and 100 μg/L for FABP often under 5 hours after an AMI (Van Nieuwenhoven et al., *Circulation* 2848-54 (1995); Wodzig et al., *Eur. J. Clin Chem Clin Biochem* 71:135-40 (1997)). Myoglobin is a heme protein that participates in the oxygen transport in the muscle, hence any severe destruction of striated muscle may result in significant elevations of its plasma concentration. Although myoglobin has a low cardiac specificity, it has a high sensitivity for myocardial injury that makes is a useful marker for AMI when used in parallel with other cardiac markers. Recent studies show that the combined measurement of myoglobin and FABP in plasma allows the discrimination between myocardial and skeletal muscle injury with the ratios for these markers differing between heart (MYO/FABP ratio 4:5) and skeletal muscle (MYO/FABP ratio 20:70, depending on muscle type). Alternately, combined measurements of myoglobin concentrations with skeletal muscle specific markers by supplementary tests such as CK-MB, cardiac specific troponins, or carbonic anhydrase III can also be used to differentiate between myocardial and skeletal muscle damage. A potential drawback is that both markers, FABP and myoglobin, unlike other cardiac markers, are eliminated from plasma by renal clearance, which means that measurements could be inaccurate in patients with chronic renal failure. In these cases, cardiac markers concentrations should be interpreted in conjunction with the individual estimated renal clearance rates of the patients. Although both markers lack cardiac sensitivity, myoglobin has been used more often as an early AMI marker. Despite recent studies that indicate cardiac FABP may provide information superior to other markers in the early onset of ACS (Ishii et al., *Clin Chem* (2005); Chen et al., *J. Huazhong Univ Sci Technolog Med Sci* 24(5):449-51, 459 (2004)), its use in the diagnosis of myocardial injury is not unanimously accepted.

Development of a cost effective, simple and efficient assay determining whether an AMI has taken place would greatly assist health care providers in timely and accurately diagnosing AMI suspected patients. It would therefore be desirable to provide improved methods and assay compositions for AMI detection. It would also be desirable to provide better methods and assays for measuring myoglobin, as well as other assayable antigens.

SUMMARY OF THE INVENTION

Assay systems and methods are provided for detecting an target antigen in a physiological fluid.

In one aspect, the method comprises linking via a first antibody a magnetic microparticle to the target antigen in the physiological fluid; linking via a second antibody a glucose molecule to the target antigen; utilizing a magnetic field to separate the magnetic microparticle and linked target antigen from at least a portion of other components in the physiological fluid, thereby forming a test sample; and detecting the glucose in the test sample to determine the concentration of target antigen in the physiological fluid.

In a preferred embodiment, the target antigen comprises a protein or marker resulting from cardiac tissue injury, which can be used in the assessment of acute myocardial infarction. One such target antigen is myoglobin. Others include creatine kinase, fatty acid-binding protein, troponins, and glycogen phosphorylase. Representative examples of physiological fluids that may be sampled and assayed include blood, serum, and urine.

The glucose detection preferably is one that can be done rapidly and includes measuring the electrical resistance, color, or pH of the test sample. In one embodiment, the glucose detection comprise measuring light transmittance through the test sample. In another embodiment, the glucose detection comprises oxidation of the glucose to gluconic acid at a platinum electrode.

In one embodiment, the first and second antibodies comprise complementary clones of monoclonal anti-human cardiac myoglobin antibody. In one example, the second antibody comprises a monoclonal mouse anti-human cardiac myoglobin Mouse isotype IgG:908, and the first antibody comprises a monoclonal mouse anti-human cardiac myoglobin Mouse isotype IgG:4E2.

In one embodiment, the second antibody is linked to a streptavidin. In one embodiment, the streptavidin is linked to a Con-A lectin which is linked to the glucose molecule. In a specific example, the second antibody is a biotinylated anti-myoglobin antibody and the anti-myoglobin antibody is linked to streptavidin which is linked to a biotinylated Con-A lectin which is linked to the glucose molecule.

In a preferred embodiment, the magnetic microparticles comprise microspheres coated with a polymer or protein. For example, the encapsulating material can comprise albumin, avidin, or a combination thereof.

In one particular assay for detecting an AMI-indicating antigen in a physiological sample, the method includes the steps of combining the physiological sample with magnetic microparticles linked to a first biotinylated antibody, wherein the first antibody bind to a first site on the AMI-indicating antigen present in the sample; applying a magnetic field to the physiological sample to separate the linked myoglobin from the blood sample to form a test sample comprising the magnetic particle-linked AMI-indicating antigen; combining the test sample with a second biotinylated antibody, wherein the second antibody binds to a second site on the AMI-indicating antigen, and wherein the second antibody is linked to a glucose molecule; and detecting the glucose in the test sample to determine the concentration of the AMI-indicating antigen, such as myoglobin, in the physiological sample, such as blood, serum, or urine.

In another aspect, an immunoassay system is provided, which includes a first antibody linkable to an assayable protein antigen present in a physiological fluid; a magnetic microparticle linked to the first antibody; a second antibody linkable to the assayable protein antigen; and a glucose molecule linked to the second antibody.

In one particular embodiment, an immunoassay kit is provide for detecting myoglobin or another AMI-indicating antigen, which includes a first part that comprises magnetic microparticles linked to antibodies selected to be linkable to a first epitope of the myoglobin or other AMI-indicating antigen; and a second part that comprises second antibodies selected to be linkable to a second epitope of the myoglobin, wherein the second antibody is linked to a lectin that is linked or linkable to a glucose molecule or enzyme tag.

In another aspect, a method is provided for detecting a target antigen in a physiological fluid which comprises the steps of linking via a first antibody a magnetic microparticle to the target antigen in the physiological fluid; utilizing a magnetic field to separate the magnetic microparticles with the target antigen linked thereto from at least a portion of other components in the physiological fluid, thereby forming a test sample; linking via a second antibody an enzymatic tag or glucose molecule to the target antigen; and detecting, using a colorimetric method, the linked enzymatic tag or glucose molecule in the test sample to determine the concentration of target antigen in the physiological fluid.

DETAILED DESCRIPTION OF THE PREFERRED EMBODIMENT

Improved assays and methods have been developed using magnetic immunoassay technology to separate the target of interest from a fluid sample and detect minute concentrations of an assayable target antigen. In a preferred application, they are used to assess myocardial injury by indirect detection of myoglobin or another protein or marker resulting from cardiac tissue injury.

Figure 1:
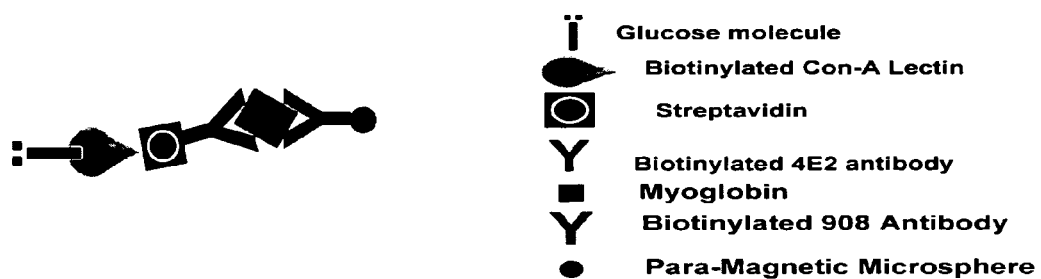
FIG. 1 is a schematic representation of one embodiment of the magnetic immunoassay described herein for detection of myoglobin.

In a preferred embodiment, the assay utilizes a magnetic solid-phase enzyme linked immunoassay (magnetic ELISA), wherein the sandwich forms by attaching two different antibodies to different epitopes on cardiac markers (i.e., an AMI-indicating antigen, such as myoglobin). One antibody is attached to a solid surface of the magnetic microsphere, and the other is attached to a glucose molecule. The first antibody is used for the separation of the AMI-indicating antigen from the physiological fluid sample whereas, the second antibody, attached to some glucose molecules, is used to measure the relative concentration of the AMI-indicating antigen in the physiological fluid. Attaching glucose molecules at the end of the anti-myoglobin antibody will further facilitate the detection of AMI because it is easily measured by a conventional glucometer. FIG. 1 shows a schematic representation of one embodiment of the magnetic immunoassay.

In other embodiments, the magnetic assay technique is adapted to separate and detect other antigens (for other uses besides AMI testing) to which two different antibodies can be attached (i.e., linked, bound) where one antibody is attached to a solid surface of a magnetic microparticle, and the other antibody is attached to a glucose molecule. Essentially any antigen (e.g., soluble protein) can be separated and detected using the appropriate antibodies linked to the magnetic microparticles and glucose molecules. In yet another embodiment, the glucose can be substituted with another sugar (e.g., mannose, fructose, galactose) that can be readily detected.

As used herein, the term "antibody" is intended to include immunoglobulin molecules and immunologically active portions of immunoglobulin molecules, i.e., molecules that contain an antigen binding site that specifically binds (immunoreacts with) an antigen, such as Fab and $F(ab')_2$ fragments. As used herein, the term "antibody" includes polyclonal and monoclonal antibodies, and variants such as single-chain (recombinant) antibodies, "humanized" chimeric antibodies, and immunologically active fragments of antibodies. For the purposes of this invention, a "chimeric" monoclonal antibody is a murine monoclonal antibody comprising constant region fragments (Fc) from a different animal. For the purposes of this invention, a "humanized" monoclonal antibody is a murine monoclonal antibody in which human protein sequences have been substituted for all the murine protein sequences except for the murine complementarity determining regions (CDR) of both the light and heavy chains. Standard techniques for the generation and isolation of antibodies are well-known and commonly employed by those of skill in the art. A number of standard techniques are described in Kohler & Milstein, *Nature* 256:495-97 (1975); Kozbor et al., *Immunol Today* 4:72 (1983); Cole et al., Monoclonal Antibodies and Cancer Therapy, pp. 77-96 (Alan R. Liss, Inc., 1985); Kenneth, in Monoclonal Antibodies: A New Dimension In Biological Analyses (Plenum Publishing Corp., New York, N.Y. 1980); Lerner, *Yale J. Biol. Med.*, 54:387-402 (1981); Gefter et al., *Somatic Cell Genet.*, 3:231-36 (1977); and Galfre et al., *Nature* 266:55052 (1977).

Complementary clones of an antibody are useful in the detection of the assayable antigen. As used herein, "complementary clones" of an antibody means antibodies that bind non-overlapping epitopes on the same antigen.

As used herein, the terms "comprise," "comprising," "include," and "including" are intended to be open, non-limiting terms, unless the contrary is expressly indicated.

Rapid Detection Method and Assay

In one aspect, an assay method is used to detect minute blood concentrations of myoglobin or another protein (e.g., creatine kinase, a fatty acid-binding protein, a glycogen phosphorylase, a troponin) indicative of AMI. In one embodiment, the assay method includes linking a first antibody linkable to an AMI-indicating antigen in a physiological sample; linking a magnetic microparticle to the first antibody; linking a second antibody to the AMI-indicating antigen; linking a glucose molecule to the second antibody; utilizing a magnetic field to separate the magnetic particle and linked AMI-indicating antigen from a portion of other components in the physiological sample, thereby forming a test sample; and detecting the glucose in the physiological sample to determine the concentration of the AMI-indicating antigen (or at least to determine the relative amount of the AMI-indicating antigen as compared to a standard or normal level of AMI-indicating antigen in the physiological fluid). In one embodiment, the glucose molecule is linked to the second antibody and the AMI-indicating antigen via a biotinylated lectin and streptavidin link. In one embodiment, the biotinylated lectin comprises a Con-A lectin. For one embodiment where myoglobin is the AMI-indicating antigen, the first antibody comprises a biotinylated 908 antibody and the second antibody comprises a biotinylated 4E2 antibody. (There also are other epitopes that can be used.) The two antibodies are bound to different epitopes on the human myoglobin or other target antigen. In another embodiment, it is possible to have a direct link between avidin or streptavidin and the glucose molecule. Con A also can be used. In one embodiment, the magnetic particles comprise microspheres coated with albumin, avidin, or a combination thereof.

In another aspect, the immunoassay for detecting myoglobin or another antigen can be provided in a kit form, similar to ELISA kits known in the art. In one example, the kit includes a first part which comprises magnetic microparticles bound to antibodies selected to be linkable to an antigen of interest; and a second part which comprises a second antibody-streptavidin-lectin, wherein the lectin is selected to be linkable to glucose and the second antibody is selected to be linkable to the antigen of interest. In a preferred embodiment, the kit includes a first part which comprises magnetic microparticles linked to antibodies selected to be linkable to a first epitope of human myoglobin; and a second part which comprises a second antibody selected to be linkable to a second epitope of human myoglobin, wherein the second antibody is linked to a lectin, which is linked to a glucose molecule.

In one embodiment of the technique, the assay method is applied to detect myoglobin or another AMI-indicating protein present in a physiological fluid (e.g., blood, serum, or urine) taken from a patient presenting a possible acute myocardial infarction. In a preferred embodiment, the physiological fluid is blood. In a preferred embodiment, a method is provided for detecting myoglobin in a blood sample which comprises: combining the blood sample with magnetic microparticles linked to a first biotinylated antibody, said first antibody binding to a first site on myoglobin present in the blood sample; combining the blood sample with a second biotinylated antibody, said second antibody binding to a second site on the myoglobin present in the blood sample, wherein said second antibody is linked to a glucose molecule; using a magnetic field and a separation process to separate the linked myoglobin from the blood sample to form a test sample comprising the myoglobin; and then detecting the glucose in the test sample, wherein the glucose detection can be correlated to the concentration of myoglobin in the blood sample.

The magnetic separation step can be conducted using techniques known in the art, for example, as taught in U.S. Pat. No. 6,132,607, which is incorporated herein by reference. In one embodiment, a separation chamber is used which comprises a plurality of magnets and a plurality of channels having an inlet and an outlet. The magnets are arranged on one side of the channels and are in contact with one another to create a magnetic field. The magnetic particle containing-fluid is introduced into the inlet of the channels of the separation chamber, and the magnetic field of the magnets captures the microparticle-attached-components within the channels and the remaining mixture exits the outlet of the channels of the separation chamber.

Glucose concentration can be measured by any of a variety of known techniques. For example, the technique can be any one of three general methods: electrical, calorimetric, or acidity measurement. In a typical glucose testing system, the following glucose reaction is utilized:

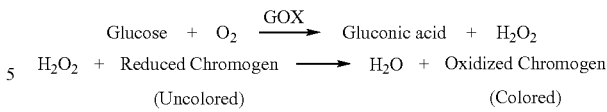

$$\text{Glucose} + \text{O}_2 \xrightarrow{\text{GOX}} \text{Gluconic acid} + \text{H}_2\text{O}_2$$
$$\text{H}_2\text{O}_2 + \text{Reduced Chromogen} \longrightarrow \text{H}_2\text{O} + \text{Oxidized Chromogen}$$
$$\text{(Uncolored)} \qquad\qquad\qquad \text{(Colored)}$$

In one embodiment, the glucose is measured electrically, based on the first part of the reaction. (See, e.g., Bennett, Blood Glucose Determination: Point of Care Testing (Available online at: http://www.sma.org/smj/97july3.htm)). In one example, reagent strips are provided having a test area impregnated with enzyme glucose dehydrogenase and two metal strips that serve as electrodes. The enzymatic action on glucose liberates an electron, which reacts with a mediator present in the strip. The monitor in which the strip is placed applies a voltage across the electrodes, causing the mediator to be reconverted to its oxidized form. This reaction generates a current proportional to the amount of glucose linked with the conjugate and is translated by the meter to a numeric glucose concentration.

Conventional glucose measurement instruments typically have a reporting range of 20 mg/dL to 600 mg/dL. Concentrations outside that range will not be detectable in such conventional glucometers. In the case of AMI, the normal concentration of myoglobin in blood varies from 32 µg/L to over than 200 µg/L, which means that the small glucose concentration in samples tested with the presently described assay methods will not be detectable by conventional glucometers. Accordingly, an alternative way to detect glucose concentration may be to measure the electrical current generated in a glucose test strip using two electrodes connected with a voltmeter, where the electrodes of the glucose test strip transfer electrical current generated from the reaction between glucose oxidase (GOX) enzyme and its substrate, glucose, from the reaction site to the glucometer. In that way, measuring the electrical current or resistance in those electrodes can be used to detect the concentration of glucose in a sample. The greater the current, the greater the concentration of the attached glucose.

In a colorimetric approach, glucose reacts with its enzyme glucose oxidase (GOX) to form gluconic acid and hydrogen peroxide ($H_2O_2$). The hydrogen peroxide then reacts with a chromogen to form a pink-colored compound, which can be monitored by reflectance photometry (Vote et al., *Clinica Chimica Acta.* 305(1-2):81-87 (2001)).

In a third approach to glucose detection, a conventional pH meter is used to detect the acidity of a sample solution, where the acidity, in the form of gluconic acid, results from the reaction between glucose and its enzyme. The acidity of gluconic acid then can be detected by a conventional pH meter, whereby a more acidic test solution indicates that more glucose is attached to the conjugate.

Those skilled in the art can readily compare the glucose concentration to a standard or target value for a particular antigen, in order to obtain useful information. In a preferred embodiment, a doctor, paramedic, or emergency room worker can take a small blood sample from a patient who is presenting a possible AMI, test the sample with the magnetic immunoassay described herein to test the patient's myoglobin level.

For diabetics suffering from AMI, a reference glucose concentration in the blood stream can be used to adjust for the glucose concentration used to measure the levels of AMI-indicating antigen in the blood.

In another aspect of the immunoassay, an enzyme tag is used instead of the glucose. For example, an enzymatic reaction such as one involving alkaline phosphatase can be used to generate a change in color which can be used to detect for the concentration of cardiac markers in a physiological fluid. That is, the enzyme tag produces a color change when reacted, so that a colorimetric technique can be used to detect or measure the pathogen in the same way that colorimetric-based glucometer would be used with a glucose-induced color change.

The magnetic microparticles facilitate separation and detection of the target antigen. As used herein, the term "magnetic microparticles" includes magnetic, paramagnetic, superparamagnetic ferromagnetic and ferrimagnetic materials. The microparticles may comprise iron, nickel, cobalt, gadolinium, manganese and/or their alloys. In one embodiment, the microparticles comprise an iron oxide, such as magnetite, or more preferably, maghemite ($\lambda Fe_2O_3$). In other embodiments, the magnetic nanoparticles comprise an alloy or a mixture of elemental materials.

The microparticles preferably are in the form of microspheres. In preferred embodiments, the microspheres have a diameter of 500 nm or less.

In a preferred embodiment, the microspheres have a magnetic core, preferably of a superparamagnetic material, with a size of about 30 nm or less, which is encapsulated with a polymer or protein. In one embodiment, the magnetic particles comprise microspheres coated with albumin, avidin, or a combination thereof. In various embodiments, the magnetic particles may be encapsulated as described in U.S. Application Publication No. 2004/0065969 to Chatterjee, et al. and U.S. Application Publication No. 2004/0146529 to Chen, et al. The disclosures of these publications are expressly incorporated by reference herein.

The methods and compositions can be further understood with the following non-limiting examples.

EXAMPLE 1

Magnetic Immunoassay for Myoglobin

Materials Preparation

Magnetic microspheres (MMS) were produced using protocols that were established by Haik, et al., *J. Magnetism & Magnetic Materials* 194:254-61 (1999); Chatterjee et al., *J. Magnetism & Magnetic Materials* 257:113-18 (2003). The MMS were coated with albumin and coupled with avidin to conjugate the anti-myoglobin antibody. The synthesis of the magnetic microspheres was accomplished according to a published protocol (Chatterjee et al., *J. Magnetism & Magnetic Materials* 257:113-18 (2003)) in three major steps: coprecipitation of ferrous chloride and ferric chloride by sodium hydroxide, material heating and sonication, and material peptization with nitric acid. Both ferrous and ferric chloride were dissolved in a 1:2 molar ratio in distilled water. The solution then was mixed immediately with a highly concentrated sodium hydroxide, stirred continuously, heated to 90° C., and sonicated to produce ultra fine magnetic particles, which then were peptized by nitric acid. Finally, the microspheres were coated with albumin and avidin to make them attachable to the biotinylated antibodies.

The antibodies used were two complementary clones of monoclonal mouse anti-human cardiac myoglobin (Mouse isotope IgG: 908 and 4E2). These clones were chosen because their epitopes are placed widely apart on the myoglobin protein. Both antibody clones were purchased from Research Diagnostics, Inc.

Both antibodies were biotinylated using an EZ-link Sulfo-NHS-LC biotinylation kit obtained from Pierce Chemicals (Rockford, Ill., USA). Long chain arm biotin containing a 22 Armstrong spacer arm between the reacted primary amine and the biotin moiety was selected to minimize the possible effects of steric hindrance when conjugating the biotin to the much larger MMS and to increase the sensitivity.

Streptavidin (SA) is a 60,000 Dalton protein composed of four identical subunits, each of which has a binding site for biotin. Isolated from the microorganism *Streptomyces avidinii*, this protein resembles egg white avidin in its biotin binding properties. Its affinity for biotin is several orders of magnitude lower than egg white avidin; it lacks carbohydrate, and has a lower isoelectric point than avidin. Streptavidin generally requires a longer spacer arm between the biotin residues and the protein or probe to which it is attached and it is less stable than avidin. The SA was obtained from Vector Laboratories (Burlingame, Calif.).

Con A is one of the most widely used and well-characterized lectins. It has broad applicability primarily because it recognizes a commonly occurring sugar structure, α-D-mannose and α-D-Glucose through its four saccharide binding sites. At neutral and alkaline pH, Con A exists as a tetramer of four identical subunits of approximately 26,000 Daltons each. Below pH 5.6, Con A dissociates into active dimers of 52,000 Daltons. The biotinylated Con A lectins also were obtained from Vector Laboratories.

Coupling Anti-Myoglobin Antibody Clone 908 to Avidin Coupled Microspheres:

One milliliter of (0.1 mg/ml) 908 biotinylated antibody solution was combined with 7.6 ml of (0.01 g/ml) avidin coupled microsphere solution. Using the HABA method to determine the minimum number of biotin groups on both antibody clones, a minimum of 15 biotin groups/antibody gives 10 nmoles of avidin needed to couple with 0.1 mg of 908 antibodies. Each 0.076 g of avidin coupled microsphere solution has 10 nmoles avidin or 7.6 ml of solution at 0.01 g/ml. The final solution of 908 antibodies and avidin-coupled microspheres were incubated while mixing at 30° C. for 30 minutes.

Coupling Anti-Myoglobin 4E2 with Glucose Molecule:

To reach the optimal performance between the reactants, concentrations of 5 µg/ml of biotinylated anti-myoglobin 4E2, 1 µg/ml of Con-A, 20 µg/ml of SA, and 5 mg/ml of glucose were prepared according to the recommendation of Suter et al., *Molecular Immunology* 26:221-30 (1989). Con-A and SA were added to attach each other in an eppendorf tube in a volume of 200 µl of each and incubated at 30° C. for 30 minutes while mixing. Then, 200 µl of biotinylated 4E2 antibodies were added to the previous solution and incubated for an additional 30 minutes at 30° C. while mixing to bind with the SA. Next, 200 µl of (5 mg/ml) glucose was added to the mixture and incubated for another 30 minutes at 30° C. while mixing to be adhered to the Con-A lectin surface.

Determination of Samples' Sizes:

Normal myoglobin concentration in the blood stream of a human patient ranges from 32 µg/L to over 200 µg/L (Hedges et al, *Ann Emerg Med,* 21:1445-50 (1992); Marcello et al., *Int'l J. Cardiology* 65(Suppl.1):S17-S22 (1998); Mauro Panteghini, *Clinica Chimica Acta* 272(1,6):23-31 (1998)). A discriminator value of 100 µg/L myoglobin was chosen as indicative of AMI (Mauro Panteghini, *Clinica Chimica Acta* 272(1,6):23-31 (1998)). It was determined that if a discriminating concentration of 100 µg/L of myoglobin containing $5.55 \times 10^{-3}$ nmoles antibody, then 0.833 µg of antibodies are needed to bind to all possible epitopes. Using 2.4 excess, which is 2.4 times the needed amount of antibody, a test amount of 2 μg of antibody needed/myoglobin sample of 100 μg/L. The amounts used were 170 μL microsphere labeled 908 antibody solution (0.0116 μg/μL) and 200 μL of (5 μg/ml) 4E2 antibody solution.

An excess amount of antibody solution was used to assure those concentrations larger than the discriminator value could be detected. Any concentration smaller than the discriminator value can be measured as the excess labeled is washed away during the immunoassay.

Experimental Procedure and Results:

After preparing the necessary components in their appropriate concentrations—(1 μg/ml) Con-A, (20 μg/ml) SA, (5 μg/ml) biotinylated 4E2 antibody, (0.0116 μg/μL) biotinylated 908 antibody, (100 μg/ml) myoglobin, and (5 mg/ml) glucose solution—an exact volume amount of 200 μl of Con-A and SA were mixed together in an eppendorf tube and incubated for 30 minutes at 30° C. while mixing in order to link them together. Then, the same volume amount of biotinylated 4E2 antibody was added to the tube and incubated under the same conditions. Finally, a glucose solution of the same amount was added to the mixture and treated in the same way to obtain the whole conjugate of (4E2 antibody-SA-Con A complex).

The second part of the ELISA conjugate, the 908 antibodies-MMS, was prepared by adding 1 ml of biotinylated 908 antibodies to 7.6 ml of (0.01 mg/ml) of MMS and incubated together for 30 minutes at 30° C. while mixing. Then, 200 μl of (100 μg/ml) myoglobin was added to the 908 antibodies-SPM complex and incubated under the same conditions.

Next, the two parts were added together and incubated in the same way. Then, two 1.5 Tesla magnets were applied to the side of the tube to isolate the reactants (MMS-908-Myo-4E2-SA-Con A-glucose) from other unneeded solution components. The isolated reactants were then washed several times with Tris Buffered Saline (TBS) while the magnets were applied.

Figure 2:
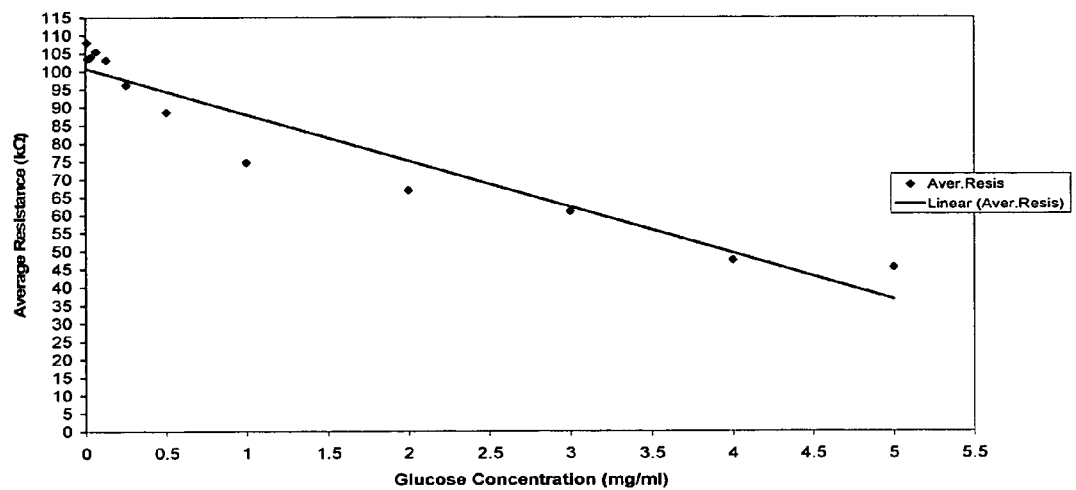
FIG. 2 is a graph of glucose concentration versus average electrical resistance in one test example.
Figure 3:
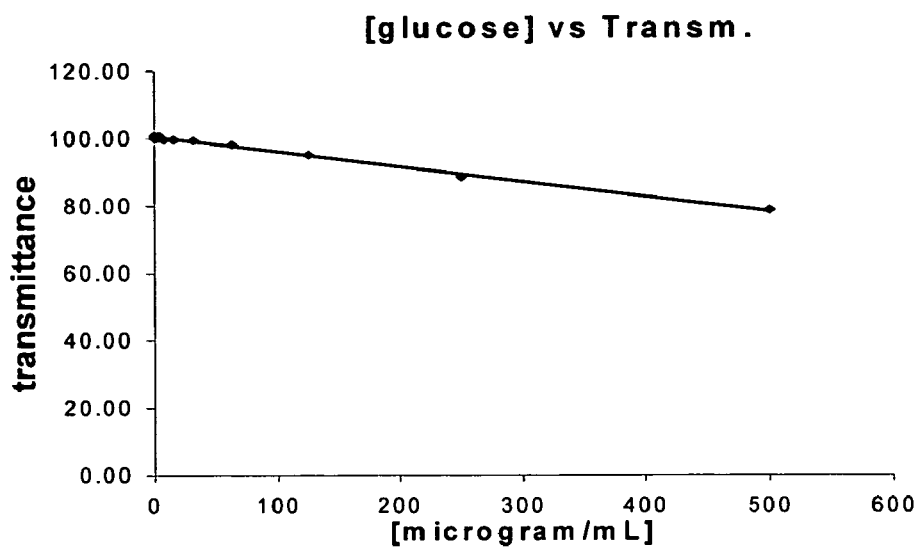
FIG. 3 is a graph of glucose concentration versus light transmittance in one test example.
Figure 4:
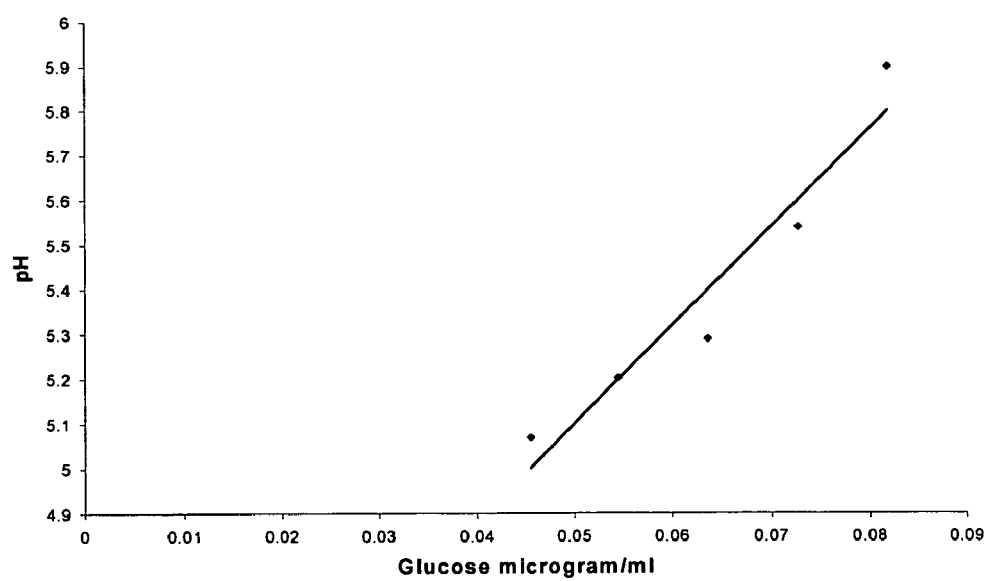
FIG. 4 is a graph of glucose concentration versus pH in one test example.

Glucose tests were then performed to measure the amount of glucose taken up by the conjugate. Electrical, colorimetric, and acidity glucose determination approaches were used. In the electrical approach, a sample volume of 5 μL of each myoglobin concentration was applied to a regular strip of an electrical glucometer (Therasense Freestyle, Ultra One Touch model) to measure the electrical resistance generated due to the reaction between glucose oxidase (GOX) enzyme and its substrate, where glucose was measured using two electrodes connected to a voltmeter (type Fluke 23). The readings showed that the electrical resistant generated in strips is inversely related to the different glucose concentration; the highest concentration had the lowest resistant (FIG. 2). In the colorimetric assay, a volume of 600 μL of glucose oxidase reagent solution was warmed for 5 minutes in a water bath under 37° C. and then a 50 μL of sample solution of each concentration of myoglobin was added to the preheated reagent solution and incubated for 10 minutes in a water bath under 37° C. The samples then were measured using a spectrophotometer, and the resulted solution had different intensities of pink color depicting the amount of glucose in each sample (see FIG. 3). In the acidity approach, a sample of 500 μL of glucose oxidase enzyme was added to a sample of 1 ml of each myoglobin concentration and allowed to react for 5 minutes to form gluconic acid solution, and then a pH meter was used to measure the acidity of each sample. Readings showed a proportional relationship between each glucose concentration and its pH level. The higher glucose concentration had the higher acidity level (see FIG. 4).

Publications cited herein and the materials for which they are cited are specifically incorporated by reference. Modifications and variations of the methods and devices described herein will be obvious to those skilled in the art from the foregoing detailed description. Such modifications and variations are intended to come within the scope of the appended claims.

I claim:

1. A method for detecting a target antigen in a physiological fluid comprising:
    linking via a first antibody a magnetic microparticle to the target antigen in the physiological fluid;
    utilizing a magnetic field to separate the magnetic microparticle and linked target antigen from at least a portion of other components in the physiological fluid, thereby forming a test sample;
    linking via a second antibody a glucose molecule to the target antigen; and
    detecting the glucose in the test sample to determine the concentration of target antigen in the physiological fluid.

2. The method of claim 1, wherein the target antigen comprises a protein or marker resulting from cardiac tissue injury.

3. The method of claim 1, wherein the target antigen comprises myoglobin.

4. The method of claim 1, wherein the target antigen is selected from the group consisting of creatine kinase, fatty acid-binding protein, troponins, and glycogen phosphorylase.

5. The method of claim 1, wherein the physiological fluid comprises blood, serum, or urine.

6. The method of claim 1, wherein the glucose detection comprises measuring the electrical resistance, color, or pH of the test sample.

7. The method of claim 1, wherein the glucose detection comprise measuring light transmittance through the test sample.

8. The method of claim 1, wherein the glucose detection comprises oxidation of the glucose to gluconic acid at a platinum electrode.

9. The method of claim 1, wherein the second antibody is linked to a streptavidin.

10. The method of claim 9, wherein the streptavidin is linked to a lectin which is linked to the glucose molecule.

11. The method of claim 1, wherein the second antibody is a biotinylated anti-myoglobin antibody and the anti-myoglobin antibody is linked to streptavidin which is linked to a biotinylated Con-A lectin which is linked to the glucose molecule.

12. The method of claim 1, wherein the first and second antibodies comprise complementary clones of monoclonal anti-human cardiac myoglobin antibody.

13. The method of claim 12, wherein the second antibody comprises a monoclonal mouse anti-human cardiac myoglobin Mouse isotope IgG:908.

14. The method of claim 12, wherein the first antibody comprises a monoclonal mouse anti-human cardiac myoglobin Mouse isotope IgG:4E2.

15. The method of claim 1, wherein the magnetic microparticles comprise microspheres coated with a polymer or protein.

16. The method of claim 15, wherein the coating comprises albumin, avidin, or a combination thereof.

17. A method for detecting an Acute Myocardial Infarction-indicating antigen in a physiological sample comprising:
    combining the physiological sample with magnetic microparticles linked to a first biotinylated antibody, said first antibody binding to a first site on the AMI-indicating antigen present in the sample;

applying a magnetic field to the physiological sample to separate the linked Acute Myocardial Infarction-indicating antigen from the blood sample to form a test sample comprising the magnetic particle-linked AMI-indicating antigen;

combining the test sample with a second biotinylated antibody, said second antibody binding to a second site on the Acute Myocardial Infarction-indicating antigen, wherein said second antibody is linked to a glucose molecule; and detecting the glucose in the test sample to determine the concentration of AMI-indicating antigen in the blood sample.

18. The method of claim 17, wherein the physiological sample is blood, serum, or urine.

19. The method of claim 17, wherein the Acute Myocardial Infarction-indicating antigen comprises myoglobin.

20. The method of claim 17, wherein the glucose detection comprises measuring the electrical resistance, color, or pH of the test sample.

21. The method of claim 17, wherein the glucose detection comprises oxidation of the glucose to gluconic acid at a platinum electrode.

22. The method of claim 17, wherein the second antibody is a biotinylated anti-myoglobin antibody and the anti-myoglobin antibody is linked to streptavidin which is linked to a biotinylated Con-A lectin which is linked to the glucose molecule.

23. The method of claim 17, wherein the first and second antibodies comprise complementary clones of monoclonal anti-human cardiac myoglobin antibody.

24. The method of claim 17, wherein the second antibody comprises a monoclonal mouse anti-human cardiac myoglobin Mouse isotope IgG:908.

25. The method of claim 17, wherein the first antibody comprises a monoclonal mouse anti-human cardiac myoglobin Mouse isotope IgG:4E2.

26. The method of claim 17, wherein the microparticles are microspheres which comprise a core of a superparamagnetic material coated with a protein or polymer.

27. A method for detecting a target antigen in a physiological fluid comprising:

linking via a first antibody a magnetic microparticle to the target antigen in the physiological fluid;

utilizing a magnetic field to separate the magnetic micro particle with the target antigen linked thereto from at least a portion of other components in the physiological fluid, thereby forming a test sample;

linking via a second antibody a glucose molecule to the target antigen; and detecting, using a colorimetric method, the linked glucose molecule in the test sample to determine the concentration of target antigen in the physiological fluid.

28. The method of claim 27, wherein the target antigen is myoglobin.

* * * * *